(12) United States Patent
Charter et al.

(10) Patent No.: US 7,410,755 B2
(45) Date of Patent: Aug. 12, 2008

(54) ADP DETECTION USING AN ENZYME-COUPLED REACTION

(75) Inventors: Neil Charter, Newark, CA (US);
Richard M. Eglen, Los Altos, CA (US);
Rajendra Singh, San Jose, CA (US);
Edwin F. Ullman, Atherton, CA (US)

(73) Assignee: Discoverx, Fremont, CA (US)

( * ) Notice: Subject to any disclaimer, the term of this patent is extended or adjusted under 35 U.S.C. 154(b) by 0 days.

(21) Appl. No.: 11/357,325

(22) Filed: Feb. 17, 2006

(65) Prior Publication Data

US 2006/0199238 A1 Sep. 7, 2006

Related U.S. Application Data

(60) Provisional application No. 60/655,536, filed on Feb. 22, 2005.

(51) Int. Cl.
*C12Q 1/00* (2006.01)
*C12Q 9/04* (2006.01)
*C12Q 1/26* (2006.01)
*C12Q 1/30* (2006.01)
*C12N 9/00* (2006.01)

(52) U.S. Cl. .................. 435/4; 435/188.5; 435/190; 435/25; 435/27

(58) Field of Classification Search .............. None
See application file for complete search history.

(56) References Cited

U.S. PATENT DOCUMENTS 4,246,342 A * 1/1981 Misaki et al. ............. 435/25
2004/0236244 A1 * 11/2004 Allen et al. ............... 600/532

* cited by examiner

*Primary Examiner*—Jon P Weber
*Assistant Examiner*—Paul C. Martin

(57) ABSTRACT

Methods and compositions are provided for determining ADP in the presence of ATP. These comprise including among the assay reagents at least one of the correcting components creatine phosphokinase and phosphocreatine, pyruvate kinase and phosphoenolpyruvate, peroxidase and a non-interfering peroxidase substrate, and catalase. One aspect of the method employs formation of hydrogen peroxide from the ADP by pyruvate kinase, phosphoenolpyruvate and pyruvate oxidase. The hydrogen peroxide is then determined. A combined reagent having all of the reagents may optionally include a peroxidase when the hydrogen peroxide is to be enzymatically determined. A peroxidase substrate is added to the sample in conjunction with the peroxidase substrate reagent, the mixture incubated and depending on whether the peroxidase substrate is a fluorescer or chemiluminescer, the mixture may be illuminated with excitation light and the emitted light determined as a measure of the ADP in the sample.

6 Claims, 5 Drawing Sheets

ADP DETECTION USING AN ENZYME-COUPLED REACTION

CROSS-REFERENCE TO RELATED APPLICATIONS

This application claims priority from U.S. Provisional Patent Application No. 60/655,536, filed Feb. 22, 2005, entitled "ADP Detection Using an Enzyme-Coupled Reaction," which is hereby incorporated by reference in its entirety.

STATEMENT OF GOVERNMENTAL SUPPORT

None.

REFERENCE TO SEQUENCE LISTING

None.

BACKGROUND OF THE INVENTION

1. Field of the Invention

The field of this invention is assays for detecting ADP presence and formation.

2. Related Art

ATP is ubiquitous as the major power source for live organisms. ATP is used with enzymes referred to as ATPases, such as with kinases for phosphorylating proteins, for glycogenesis, and for metabolizing sugars and fats, to name only a few. In trying to discern cellular pathways and the effect of changes in the environment on these pathways, the ability to measure the amount of ADP is advantageous. Also, one may be interested in the amount of ATP in a sample, particularly where the ATP is to be monitored by the formation of ADP.

One approach for measuring ADP is to use an enzyme-coupled reaction in order to produce a readily detectable signal. Since, in many of the contexts in which one wishes to measure ADP, the amount of ADP will be very small or one will be interested in small differences in the amount of ADP between determinations, sensitive detection becomes an important factor.

In the literature, there has been a description of an enzyme-coupled reaction to determine ADP. In this method, pyruvate kinase and phosphoenolpyruvate are combined in the assay mixture and react with ADP to form ATP and pyruvic acid. Also included are pyruvate oxidase and its cofactors FAD and TPP, which transform the pyruvate to acetyl phosphate and hydrogen peroxide. The hydrogen peroxide is then detected by catalyzing its reaction with the fluorescent dye, Amplex® Red (a fluorescent dye) using horseradish peroxidase.

While the method would appear to be highly sensitive, it suffers from the problems of contamination of the various materials used in the process. Phosphoenolpyruvate spontaneously hydrolyzes to give pyruvic acid, which is involved as an intermediate in the production of hydrogen peroxide. Any adventitious pyruvic acid will result in an augmented determination, indicating a larger amount of ADP than was present. Also, buffers and assay components may be contaminated with hydrogen peroxide. The substrates one employs as the detectable species and other components of the assay may also produce hydrogen peroxide. The method therefore suffers from the potential for numerous introductions of intermediates that will alter the result and provide for erroneous determinations. In addition, it is well known that ATP will spontaneously hydrolyze to ADP and phosphate, so that the ATP may be contaminated to varying degrees with ADP depending upon the manner in which the ATP is prepared, stored and handled. Since adventitious presence of ADP in the assay mixture will substantially compromise the assay, it is important to minimize the amount of ADP present from other than the reaction of interest.

In developing an assay for commercialization, there are a number of considerations that guide the protocol employed. Desirably, the maximum number of agents employed in the assay is combined as a single reagent, so as to minimize the number of measurements and additions that must be performed. The greater the number of measurements and additions that must be performed, the greater the errors that are likely to be produced. Particularly, where an assay requires a large number of reagents, it is especially desirable to be able to combine them in large amounts and mix the reagents homogeneously, so that they are accurately measured in the proper proportions and can dissolve and rapidly interact during the assay.

Because of the importance of the determination of ADP, providing for an accurate, reasonably rapid method of measurement, where one can use the protocol in both medium and high throughput screening, is very desirable.

Relevant Literature

An abstract presented at the SBS 2002 meeting on Sep. 22-26, 2002, by Juan-Manuel Dominguez, et al., in the section Novel Detection Technologies and Assay Formats, ID:2322, states: "A new fluorogenic method for the detection of ADP is described. It is based on the sequential action of pyruvate kinase and pyruvate oxidase to generate hydrogen peroxide, which is utilized by peroxidase to convert non-fluorescent Amplex® Red (a fluorescent dye) into fluorescent resorufin. The method is amenable to on-line kinetics and has proved to be very sensitive, capable of detecting 1 micromolar ADP, and thus suitable to be used to measure kinase activities. To support this idea, bacterial thymidylate kinase has been screened using this method to monitor enzyme activity against a collection of 500,000 compounds. Z-prime values were consistently maintained around 0.80 throughout the whole campaign. As a result, potent inhibitors of the enzyme have been found, yielding IC50 values in the nanomolar range."

Also of interest are Finer et al., U.S. Pat. No. 6,410,254, Eiji, et al., "Pyruvate oxidase, its preparation and use," EPA 0,274,425 and Kiianitsa, et al., "NADH-coupled microplate photometric assay for kinetic studies of ATP-hydrolyzing enzymes with low and high specific activities," 2003 Analytical Biochemistry 321:266-271. Japanese Application Publication Number 61-092598, or Application Number 59-214386, "Method of Determining ADP," describes an ADP assay using pyruvate kinase and pyruvate oxidase.

BRIEF SUMMARY OF THE INVENTION

Methods and reagents are provided for performing ADP determinations while minimizing adventitious contamination of the assay medium introducing erroneous results. The method employs ATP as a source of ADP, which may be combined with pyruvate kinase, phosphoenolpyruvate, pyruvate oxidase, FAD, TPP, peroxidase and a peroxidase substrate that becomes detectable when oxidized by hydrogen peroxide. Introduction of errors resulting from contamination of components of the assay is diminished by desirably having at least one of the following: the ATP mixed with a reagent that reacts with ADP; phosphoenolpyruvate mixed with a reagent that reacts with pyruvate; and components subject to being contaminated with hydrogen peroxide mixed with a reagent that reacts with hydrogen peroxide, usually a catalase. When the assay is used to determine the ADP produced in a reaction, it may be performed in two stages. An endpoint assay can be performed by stopping the ADP forming reaction and then determining the ADP as a function of the amount of hydrogen peroxide that is formed. Alternatively a kinetic assay can be performed by combining all the reagents in a single step followed by determining the ADP as a function of the rate of formation of hydrogen peroxide

DETAILED DESCRIPTION OF THE PREFERRED EMBODIMENT

Overview

Figure 1:
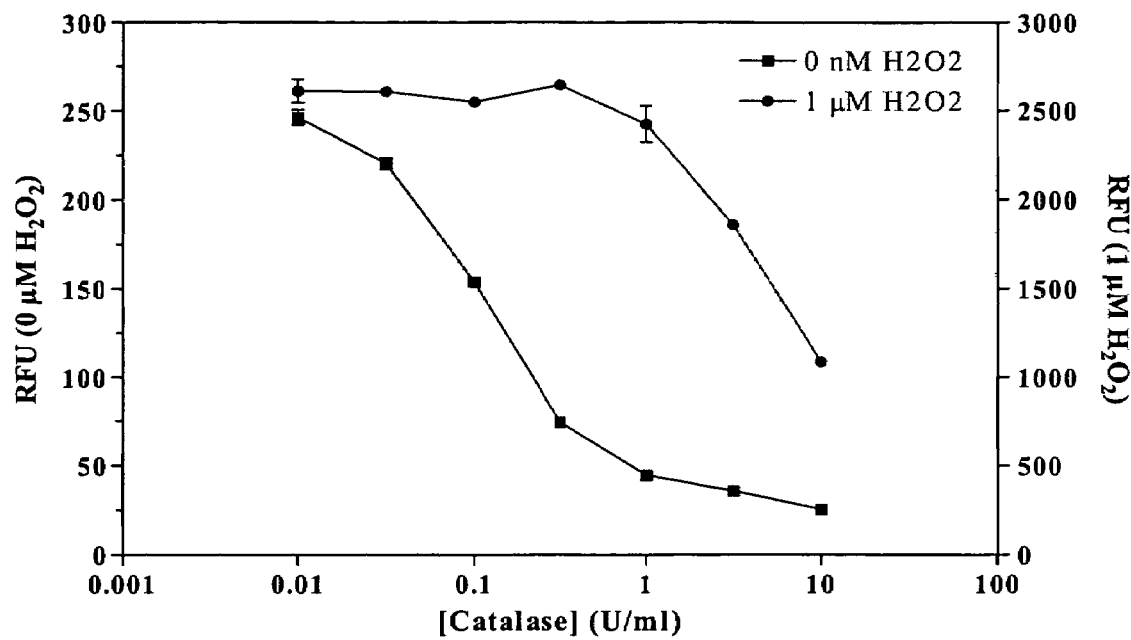
FIG. 1 is a graph showing effect of catalase concentration on assay signal and background.

Methods and compositions are provided for improved detection of ADP (adenosine diphosphate) by eliminating interfering assay components. Of particular interest are assays that use an enzyme-coupled reaction to produce a signal related to the amount of ADP present in the assay medium. The method employs forming pyruvate from ADP using pyruvate kinase and phosphoenolpyruvate, oxidizing the pyruvate with pyruvate oxidase to give hydrogen peroxide and then detecting the peroxide by any convenient means as a determination of the amount of ADP.

The method employs correcting components that serve to reduce adventitious contributors to erroneous results. The adventitious contributors result from normal processes of hydrolysis, oxidation, and the like to produce intermediates involved in the determination of ADP that result from other than the ADP produced as a result of the event of interest. Of particular concern are ADP resulting from the hydrolysis of ATP, pyruvate resulting from the hydrolysis of phosphoenolpyruvate and hydrogen peroxide that can come from a variety of sources associated with the determination.

Interfering amounts of ADP present from sources other than the determination of interest can be diminished by including pyruvate kinase and phosphoenolpyruvate or creatine phosphokinase and phosphocreatine with the source of interfering ADP. Particularly, ATP is found to hydrolyze to ADP under varying conditions, particularly during storage. By storing the ATP reagent with small amounts of creatine phosphokinase and phosphocreatine that will not interfere with the assay, the background resulting from adventitious ADP can be substantially diminished. If desired, some time prior to performing the determination, for example, at least about 3 hrs, preferably at least about 6 hrs, the correcting agents described above may be added to the ATP in amounts that when the assay is performed, they will not interfere with the assay. The former correcting agents will not interfere as being part of the reagent combination for the determination.

Phosphoenolpyruvate can be a source of pyruvate, particularly during storage. By including with the phosphoenolpyruvate as correcting agents a small amount of lactate dehydrogenase (LDH) and reduced nicotinamide adenine dinucleotide (NADH), pyruvate will be reduced to lactate, a non-interfering substance. By storing the phosphoenolpyruvate source with LDH and NADH in amounts that will not interfere with the assay when the phosphoenolpyruvate reagent is present in the assay mixture, the background resulting from adventitious pyruvate can be substantially diminished. Alternatively, pyruvate may be removed by storing the phosphoenolpyruvate with glutamic pyruvic transaminase and glutamic acid, which converts the pyruvate to alanine or with pyruvate oxidase to convert the pyruvate to acetylphosphate, carbon dioxide and hydrogen peroxide. A hydrogen peroxide scavenger, such as catalase, can be included to decompose the resulting hydrogen peroxide prior to use of the reagents.

Various components used in the assay may be a source of adventitious hydrogen peroxide. The hydrogen peroxide present in such components may be substantially diminished by having a non-interfering amount of a hydrogen scavenger substance, for example, with catalase-like activity present to react with the hydrogen peroxide to form water, a non-interfering product. Alternatively adventitious hydrogen peroxide can be removed using a peroxidase together with a peroxidase substrate that does not interfere with the assay. For example a water-soluble non-chromogenic substrate may be used such as a mono- or diacylhydrazide or -semicarbazide, or hydroquinone such as gentisic acid.

When the hydrogen peroxide produced in the assay is to be determined by causing it to oxidize a leuco dye or a peroxidase substrate dye precursor, there may be included with such reagent, an agent, e.g., uv absorber or radical chain inhibitor, to prevent degradation of the leuco-dye or substrate.

It is found that one may use one or more of the agents to reduce background in substantially non-interfering amounts that will not prejudice the results obtained with the assay. By substantially non-interfering is intended that the difference in the observed results in the presence of the correcting components and in their absence with non-contaminated reagents is less than about 20%, usually less than about 10%.

The sample may be derived from a variety of sources. Primarily, the subject assay when using ATPases will be concerned with substantially pure samples of one or more ATPases. However, there may be situations where other proteins may be present. For example, organelles or cell lysates may be analyzed as to their rate of ADP production.

The assay will usually be carried out in small volumes ranging from about 5 to 500 µl, more usually from about 10 to 100 µl. Conveniently, microtiter well plates may be used that range from about 96 to 1536 wells or more, more usually from 96 to 384 wells. Depending on the nature of the determination, the wells may be opaque. The temperature for the assay will generally be in the range of about 10 to 40° C., more usually in the range of about 20 to 40° C. The time for the assay will depend upon the reaction, if any, being monitored. Generally, when the ADP is being produced by an enzyme reaction, the time for the reaction will be at least about 5-180 min, more usually about 10-60 min. For measurement of the kinetics of ADP production, one will add all of the reagents for producing the ADP and monitoring its concentration and follow the course of the reaction. For determination of a fixed concentration of ADP or determination of the endpoint of a reaction that produces ADP, when the time for the ADP production has been completed, the reagents are added and a reading taken immediately or the mixture incubated for a period of up to 24 hrs or more prior to taking a reading.

The order of addition of the components will vary depending upon how many of the components have been precombined for simultaneous addition and whether the assay is an endpoint assay or a kinetic assay. The reagents can be stored in solution at reduced temperatures, generally below about −10° C., preferably at or below −20° C. and thoroughly thawed prior to use. Alternatively, if convenient, the reagent solutions may be prepared prior to use from dry (e.g., lyophilized) or concentrated stock preparations and then used within a short time of preparation, usually fewer than about 24 h. Where it is impracticable to prepare the reagents in bulk, the individual components may be combined simultaneously or sequentially, either prior to the addition to the sample or at the time of addition.

The amounts of the various reagents in the assay mixture may be varied over moderate ranges. When the amount of ADP that is produced from ATP in an ATPase activity assay is to be determined the ATP reagent can include one or more enzymes that destroy ADP that is initially present. Creatine phosphokinase and phosphocreatine may be combined with the ATP for a sufficient time prior to the assay to reduce adventitious ADP by at least 50%, preferably 90% or more. The amount of these reagents must be sufficiently low that their effect on the rate of depletion of ADP is much less than the rate of formation of ADP from the ATP during the assay, usually under 5%. Similar considerations apply to the concentration of pyruvate kinase (PK) and phosphoenolpyruvate (PEP).

Pyruvate formed when PK and PEP are used in the enzyme coupled assay will usually be oxidized using pyruvate oxidase to provide hydrogen peroxide which can then be determined by any convenient means. The amounts of PK and PEP used for this purpose will depend on the whether an endpoint or kinetic assay is desired. A kinetic assay must include a sufficiently high concentration of PK and PEP that the ADP being formed reacts rapidly to produce pyruvate such that the rate of pyruvate formation mirrors the rate of ADP formation. Similarly, the pyruvate oxidase must be present in sufficiently high concentration that the rate of hydrogen peroxide formation mirrors the rate of pyruvate formation. By contrast, for an endpoint assay, the concentration of these reagents can be much reduced depending on the desired time for reaction of the ADP with ultimate formation of hydrogen peroxide. In general, the concentration of these reagents will be determined empirically to satisfy the desired assay characteristics.

The concentration of reagents required to determine the hydrogen peroxide produced in the reaction will depend on the desired assay protocol and the detection method. When the concentration of hydrogen peroxide is determined directly by electrochemical means no other reagent is required. For luminescence detection, various luciferases may be used, or luminescence can be generated as described in U.S. Pat. No. 6,143,514. When fluorescence detection is desired, a peroxidase and a fluorogenic peroxidase substrate can be included in the reaction mixture. The concentrations of these reagents can vary widely and may also be determined empirically to meet the desired assay characteristics. The Tables below give exemplary preferred ranges, although concentrations within these ranges may be employed. For example, the phosphoenolpyruvate may preferably also be present in a range of 20-2500 μM The following Table 1 indicates the broad range and the preferred range of each of the major reagents in the assay mixture:

TABLE 1

| Component | Broad range | Preferred range |
|---|---|---|
| Pyruvate kinase | 1-1000 U/ml | 5-500 U/ml |
| Pyruvate oxidase | 0.1-500 U/ml | 1-100 U/ml |

TABLE 1-continued

| Component | Broad range | Preferred range |
|---|---|---|
| Peroxidase | 0.1-500 U/ml | 1-100 U/ml |
| Scavenger* | 0.005-50 U/ml | 0.01-10 U/ml |
| Phosphoenolpyruvate | 1-5000 μM | 10-1000 μM |

*The concentration is given using catalase as the scavenger, which is representative of other scavengers.

Components other than those listed in the above table will usually also be present, so that the following Table 2 indicates the additional components that will usually be present and a broad and preferred range for their concentrations.

TABLE 2

| Component | Broad range | Preferred range |
|---|---|---|
| Pyruvate kinase | 1-1000 U/ml | 5-500 U/ml |
| Pyruvate oxidase | 0.1-500 U/ml | 1-100 U/ml |
| Peroxidase | 0.1-500 U/ml | 1-100 U/ml |
| Scavenger* | 0.005-50 U/ml | 0.01-10 U/ml |
| Flavin adenine dinucleotide (FAD) | 0.1-500 μM | 1-100 μM |
| Thiamine pyrophosphate (TPP) | 1-5000 μM | 10-1000 μM |
| Phosphoenolpyruvate | 1-5000 μM | 10-1000 μM |
| Buffer | 1-200 mM | 10-100 mM |
| Peroxidase substrate** | 0.1-500 μM | 10-100 μM |
| Activating salt (e.g., MgCl$_2$) | 0.1-50 mM | 0.2-40 mM |

*The concentration is given using catalase as the scavenger, which is representative of other scavengers.
**Where a fluorogenic substrate is used for detection as the peroxidase substrate.

Of particular interest is a combined reagent that can be added as a single entity. The amounts indicated are the base ratios and the ultimate composition can be any multiple thereof, while retaining the ratios of the various components. As the combined reagent, the following Table 3 indicates the broad and narrow ranges that may be employed for the key reagents. When dissolved in buffer, the below-indicated concentrations would be obtained.

TABLE 3

| Component | Broad range | Preferred range |
|---|---|---|
| Pyruvate kinase | 2-500 U/ml | 10-500 U/ml |
| Pyruvate oxidase | 0.2-200 U/ml | 2-50 U/ml |
| Peroxidase | 0.2-200 U/ml | 1-50 U/ml |
| Scavenger* | 0.01-25 U/ml | 0.02-10 U/ml |
| Phosphoenolpyruvate | 2-2500 μM | 20-800 μM |

*The concentration is given using catalase as the scavenger, which is representative of other scavengers.

For greater convenience, there would be included a number of other agents that will find common use with the above reagents. The following Table 4 is a more complete table as to what may be included in a single reagent for use in the subject determination.

TABLE 4

| Component | Broad range | Preferred range |
|---|---|---|
| Pyruvate kinase | 2-500 U/ml | 10-500 U/ml |
| Pyruvate oxidase | 0.2-200 U/ml | 2-50 U/ml |
| Peroxidase | 0.2-200 U/ml | 1-50 U/ml |
| Catalase | 0.01-25 U/ml | 0.02-10 U/ml |
| Flavin adenine dinucleotide (FAD) | 0.2-250 μM | 2-80 μM |
| Thiamine pyrophosphate (TPP) | 2-2500 μM | 20-500 μM |
| Phosphoenolpyruvate | 2-2500 μM | 20-800 μM |
| Buffer | 1-200 mM | 10-100 mM |

TABLE 4-continued

| Component | Broad range | Preferred range |
|---|---|---|
| Activating salt (e.g. MgCl$_2$) | 0.1-50 mM | 0.2-30 mM |
| Enzyme stabilizer | 1-50 wt % | 2-40 wt % |

As a detection reagent, one may employ from 1-1000 µM, more usually 5-500 µM of the peroxidase substrate in conjunction with about 0.05-50 U/ml. usually 0.1-10 U/ml of catalase.

The reagent concentrations indicated above may be enhanced 2×, 3×, 4× or more depending upon the volume used in the assay, the particular assay, and whether one wishes the minimum amount that may be used in the reagent volume or the enhanced amount for a particular assay.

Various conventional buffers may be employed in conjunction with the reagents that find application with the enzymes used in the assay. The buffers include phosphate, Hepes, Tris, MOPS, etc., at concentrations as previously indicated. The pH will be conveniently about 7, but can be varied from 5-9. For sample dilutions, where a kinase assay is involved, generally a conventional low salt buffer will be employed, using Hepes, Tris, MOPS, phosphate, etc. Other conventional additives may also be included in this buffer, such as salts at varying concentrations, e.g. 0.1-400 mM, chelating agents at concentrations in the range of about 0.1 to 100 mM, non-ionic detergents at concentrations in the range of about 0.005 to 10%, 0.1-50 mM magnesium salt (or other activating salt), and 0.05 to 10% protein. The particular buffer will be chosen in accordance with the nature of the system producing the ADP. The coenzymes that find use will be used at conventional concentrations in accordance with the amount of enzyme being used, normally in non-limiting amounts. For the combined reagents various stabilizers can be employed, such glycerol, trehalose, carrier protein (e.g. BSA), Ficoll etc., in amounts that provide the desired stability without interfering with the assay. Generally polyols will be used as the stabilizing agent.

The detection may be performed in a variety of ways, using substrates that result in a fluorescent or chemiluminescent product, electrochemically or any other means of detecting hydrogen peroxide formation. For the most part, the assay has been exemplified using light emission. Substrates that can find use include resorufin derivatives that are oxidized with peroxidase and hydrogen peroxide to emit light, such as N-acetyl dihydroresorufin (Amplex® Red (a fluorescent dye)), aryl ethers of fluorescent dyes as described in U.S. Pat. No. 4,857,455, and hydroxyphenylpropionic acid etc, where the substrate is oxidized by the action of the peroxidase and hydrogen peroxide. Commercial readers for emission are readily available, particularly readers with which microtiter well plates can be used.

For convenience, kits can be provided comprising the detection including the ATP reagent and the detection reagent, as well as buffers, enzymes, or other component that may be of use in the determining ADP. The various reagents can be provided in individual containers, particularly darkened containers for the reagents.

The subject method can be used for determining ADP in a variety of contexts. The method can be used for determining the amount of ADP in ATP, ATPase activity in a sample, protein kinase activity, kinase activity for other than proteins, such as lipid kinases and other small molecule kinases, metabolic activity requiring ATP consumption, monitoring bound versus unbound ADP, etc.

The following examples are offered by way of illustration and not by way of limitation.

EXPERIMENTAL

Assay Protocol

The current assay format is as shown below for an assay performed in a 384 well assay plate with fluorescent output:

20 µl reaction or ADP calibrator is added to a well of a black 384 well assay plate (Greiner).

Incubation at required temperature for required period of time.

Addition of 10 µl ADP Substrate Reagent immediately followed by

Addition of 20 µl ADP Enzyme Reagent
Incubation of assay for 30 minutes at room temperature.

Acquisition of assay signal using fluorescent plate reader at excitation/emission wavelengths of 530 and 590 nm respectively.

ADP Reagent Formulation

The assay is currently comprised of two reagents: ADP Enzyme Reagent and ADP Substrate Reagent.

ADP Enzyme Reagent

ADP Enzyme Reagent consists of the following components:
1 mM MgCl$_2$
25 µM FAD (Flavin Adenine Dinucleotide)
250 µM TPP (Thiamine Pyrophosphate)
250 µM PEP (Phosphoenolpyruvate)
25 U/ml HRP (Horseradish Peroxidase)
50 U/ml Pyruvate Kinase
15 U/ml Pyruvate Oxidase
1 U/ml Catalase
50 mM Sodium Phosphate buffer, pH 7.0
15% glycerol as stabilizers for enzymes ADP Substrate Reagent ADP Substrate Reagent consists of the following components:
250 µM Amplex® Red (a fluorescent dye) Peroxidase Substrate
1 U/ml Catalase
50 mM Sodium Phosphate buffer, pH 7.0.

Both reagents are stored at −20° C. For use, each reagent is thawed at room temperature and used without further dilution.

Experimental Data

Below are example assays and calibration curves performed with this assay, along with the experimental procedures used.

Reduction of Assay Interference by a Hydrogen Peroxide Scavenger

Assay sensitivity can be affected by the amount of adventitious hydrogen peroxide present in the assay reagents. To address this issue, the ability of low concentrations of hydrogen peroxide scavenger to reduce the level of hydrogen peroxide in solution is examined.

In this experiment, 50 mM phosphate buffer was treated with 0-10 units/ml of catalase for two hours at room temperature. The presence of hydrogen peroxide was detected by adding 10 µl 250 µM Amplex® Ultra Red (a fluorescent dye) (in phosphate buffer) and 10 µl horseradish peroxidase (in phosphate buffer) to 30 µl of catalase-treated phosphate buffer in wells of a black 384 well assay plate. The assay plate was covered and incubated at room temperature for 30 minutes. Assay signal was measured with a Fluorocount® fluorescent plate reader (Packard) using 0.1 second integration with excitation and emission wavelengths at 530 and 590 nm respectively and a PMT voltage of 781 Volts.

Incubation of assay reagents with catalase resulted in a dose dependent reduction of signal background (signal at 0 µM ADP) (FIG. 1). Catalase concentrations at 0.3 U/ml or above were sufficient to eliminate the majority of the interfering background signal. Since excess catalase would result in the elimination of hydrogen peroxide generated from the presence of ADP, the signal generated with 1 µM ADP was also determined. Catalase at 3 U/ml or above produced a reduction in assay signal indicating that at those concentrations of scavenger assay performance was being significantly diminished. Combined the data indicates that the addition of catalase to the reagents at 1 U/ml provided the optimal reduction of assay background without impairing performance in measuring hydrogen peroxide formation. Therefore the addition of a peroxide scavenger such as catalase provides a ready means to eliminate background signal resulting from not only the presence of hydrogen peroxide in situ but also that resulting from de novo peroxide generating components.

Calibration Curve

Prior to performing a calibration curve for the ADP Detection Assay, the assay reagents were thawed at room temperature for several hours.

Serially diluted calibrator was generated as follows: A 100 mM stock of ADP calibrator was diluted to 1 mM and then to 79 µM in Low salt assay buffer (LS ASB) consisting of 15 mM Hepes, 20 mM NaCl, 1 mM EGTA, 0.02% Tween 20, 10 mM $MgCl_2$, 0.1% bovine gamma globulin at pH 7.4.). Half-log serial dilutions of the calibrator were performed to produce calibrator reagent concentrations of 79, 25, 7.9, 2.5, 0.79, 0.25, 0.079 µM ADP. After the addition of assay reagents, the final system concentrations of the diluted calibrator was 31.6, 10, 3.16, 1, 0.316, 0.1, 0.0316 µM respectively. A control containing LS ASB only was included to determine assay background signal.

20 µ of diluted calibrator or control was added per well of a black 384 assay plate (Griener). 3 replica wells were used per calibrator concentration. 10 µl ADP Substrate Reagent was added followed immediately by 20 µl of ADP Enzyme Reagent. The assay plate was covered and incubated at room temperature for 30 minutes. Assay signal was measured with a Fluorocount® fluorescent plate reader (Packard) using 0.1 second integration with excitation and emission wavelengths at 530 and 590 nm respectively and a PMT voltage of 750 Volts.

Figure 2:
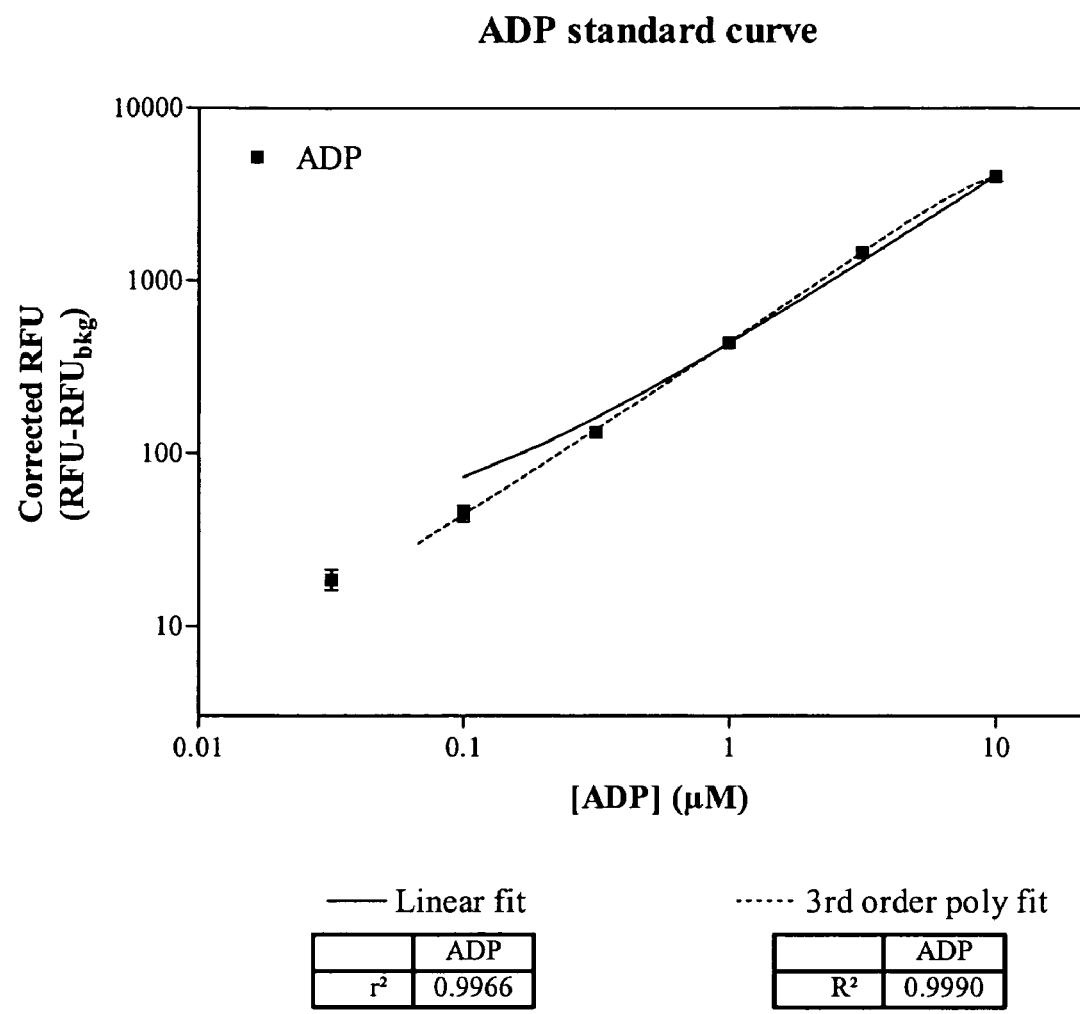
FIG. 2 is a calibration curve for determination of ADP.

A linear relationship between ADP concentration and signal was observed between 0.1 to 10 µM ADP (FIG. 2). The data shown is corrected for background by subtracting the signal obtained for the control (Mean RFU=157.3) from the values generated at varying calibrator concentrations and fitted using linear and $3^{rd}$ order polynomial regression.

Detection of Kinase Activity

An example kinase reaction is given below to demonstrate the assay dynamic range. In this experiment, the effect of ATP concentration on Protein Kinase A (PKA) activity was examined. PKA concentration was titrated in kinase reactions containing varying concentrations of ATP.

To perform a protein kinase assay using the ADP Detection Assay, the assay reagents were thawed at room temperature for several hours.

Low salt assay buffer (LS ASB) was used to dilute all reagents in the kinase reaction and consisted of 15 mM Hepes, 20 mM NaCl, 1 mM EGTA, 0.02% Tween 20, 10 mM $MgCl_2$, 0.1% bovine gamma globulin at pH 7.4. Substrate and ATP reagents were produced that containing 400 µM Kemptide substrate and 20 or 200 µM ATP. PKA kinase (Upstate) was serially diluted (half-log steps) to give reagent concentrations of 2000, 633, 200, 63.3, 20, 6.33, 2, 0.633, 0.2, 0.0633, 0.02 and 0 ng/ml. 10 µl of ATP, 5 µl of substrate and 5 µl of diluted kinase were combined in wells of a 384 well plate, covered with plate sealing tape and incubated at 30° C. for 1 hour.

To detect the generation of ADP as a result of kinase activity, 10 µl ADP Substrate Reagent was added followed immediately by 20 µl of ADP Enzyme Reagent. The assay plate was covered and incubated at room temperature for 30 minutes. Assay signal was measured with a Fluorocount® fluorescent plate reader (Packard) using 0.1 second integration with excitation and emission wavelengths at 530 and 590 nm respectively and a PMT voltage of 750 Volts.

Figure 3:
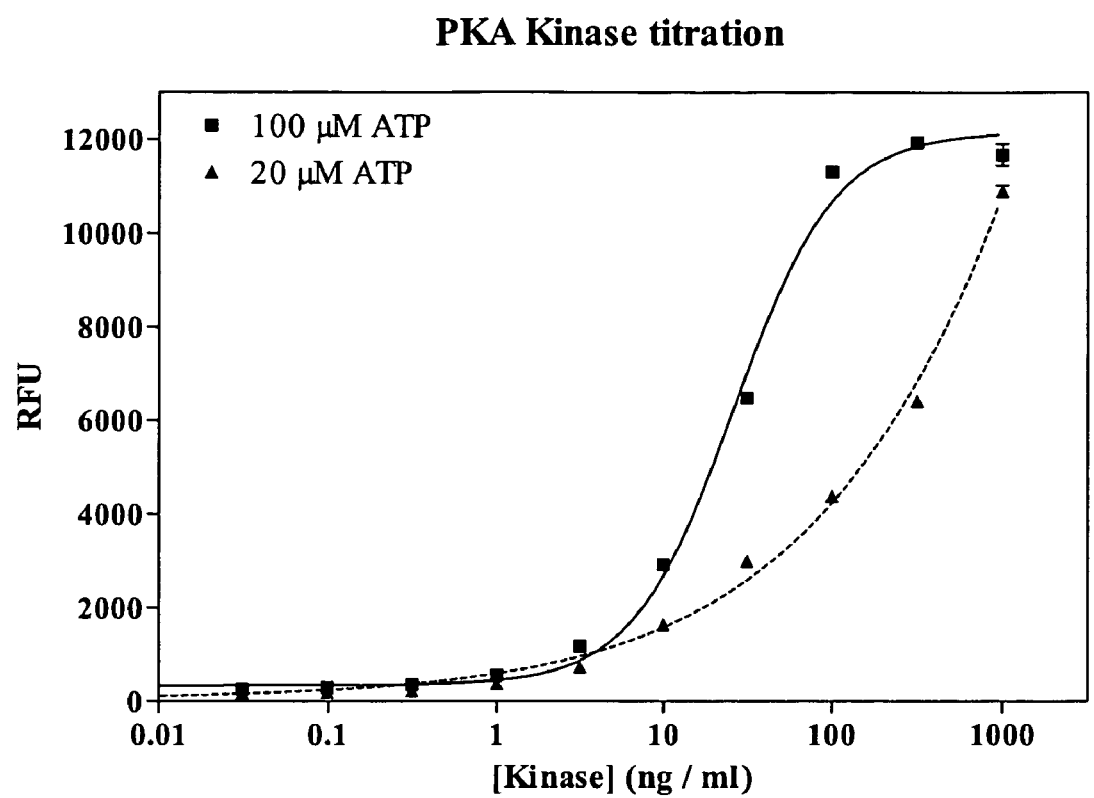
FIG. 3 is a graph of PKA activity with respect to enzyme concentration.

Titration of PKA in the kinase reaction resulted in a dose dependent increase in ADP with kinase concentration (FIG. 3). Kinase activity was dependent on ATP concentration, with lower concentrations of ATP (20 µM) resulting in a lower rate of phosphorylation. At high kinase concentrations, the assay signal reaches a plateau since product formation exceeds the detection range of the assay.

Kinetic Analysis of Kinase Activity

In this second example, kinase reaction, the activity of PKA is characterized further. In this experiment, the kinetics of ATP on PKA activity was examined by measuring the rate of kinase activity at varying concentration of ATP. The results of this assay were fitted to the Michaelis-Menten equation so that the $K_m$ (Michaelis-Menten constant) of ATP for PKA could be determined.

To perform a protein kinase assay using the ADP Detection Assay, the assay reagents were thawed at room temperature for several hours.

Low salt assay buffer (LS ASB) was used to dilute all reagents in the kinase reaction and consisted of 15 mM Hepes, 20 mM NaCl, 1 mM EGTA, 0.02% Tween 20, 10 mM $MgCl_2$, 0.1% bovine gamma globulin at pH 7.4. Substrate reagent was generated containing 800 µM Kemptide substrate. ATP was serially diluted (half-log steps) to give reagent concentrations of 400, 127, 40, 12.7, 4, 1.27, 0.4 and 0 µM ATP. PKA kinase (Upstate) was diluted to give a reagent of 20 ng/ml. 10 µl of diluted kinase and 5 µl of substrate and 5 µl of diluted ATP were combined in wells of a 384 well plate, covered with plate sealing tape and incubated at 30° C. for 1 hour.

To detect the generation of ADP as a result of kinase activity, 10 µ ADP Substrate Reagent was added followed immediately by 20 µl of ADP Enzyme Reagent. The assay plate was covered and incubated at room temperature for 30 minutes. Assay signal was measured with a Fluorocount® fluorescent plate reader (Packard) using 0.1 second integration with excitation and emission wavelengths at 530 and 590 nm respectively and a PMT voltage of 750 Volts.

The data was converted by dividing the signal measured by 60 to obtain the enzyme rate in RFU per minute. This was plotted against ATP concentration used and fitted to the Michaelis-Menten equation (Equation 1).

$$\text{Rate}=(V_{max}*[ATP])/(K_m+[ATP]). \quad \text{Equation 1}$$

Figure 4:
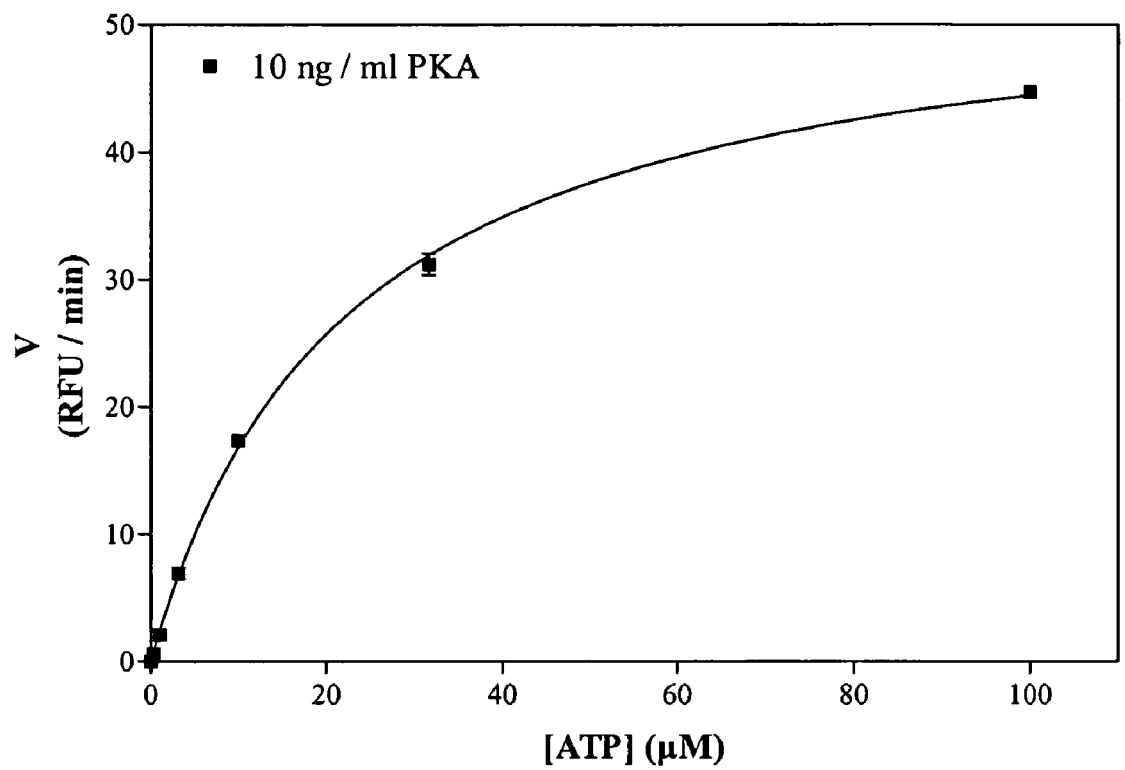
FIG. 4 is a Michaelis-Menten plot for ATP and PKA showing $V_{max}$ and $K_m$ data.

From the curve, a $K_m$ of 22.29 µM ATP and a $V_{max}$ of 54.38 were derived for PKA (FIG. 4). These values are consistent with those obtained independently (see Zimmermann et al. (1999) JBC, 274, 5370).

Analysis of Kinase Inhibitor Activity

In this third example, kinase reaction, the inhibition of PKA activity by staurosporine is examined. In this experiment, the inhibitory activity was determined by measuring kinase activity at varying concentrations of staurosporine.

To perform a protein kinase assay using the ADP Detection Assay, the assay reagents were thawed at room temperature for several hours.

Low salt assay buffer (LS ASB) was used to dilute all reagents. Substrate and ATP reagents were generated containing 100 µM Kemptide substrate or 100 µM ATP. PKA kinase (Upstate) was diluted to give a reagent of 80 ng/ml. 5 µl diluted staurosporine, 5 µl substrate and 5 µl of kinase were combined in wells of a 384 well plate and incubated for 10 minutes at room temperature. To initiate the kinase reaction, 5 µl ATP was added per well and the assay plate was covered with plate sealing tape and incubated at 30° C. for 1 hour.

To detect the generation of ADP as a result of kinase activity, 10 µl ADP Substrate Reagent was added followed immediately by 20 µl of ADP Enzyme Reagent. The assay plate was covered and incubated at room temperature for 30 minutes. Assay signal was measured with a Fluorocount® fluorescent plate reader (Packard) using 0.1 second integration with excitation and emission wavelengths at 530 and 590 nm respectively and a PMT voltage of 750 Volts.

Figure 5:
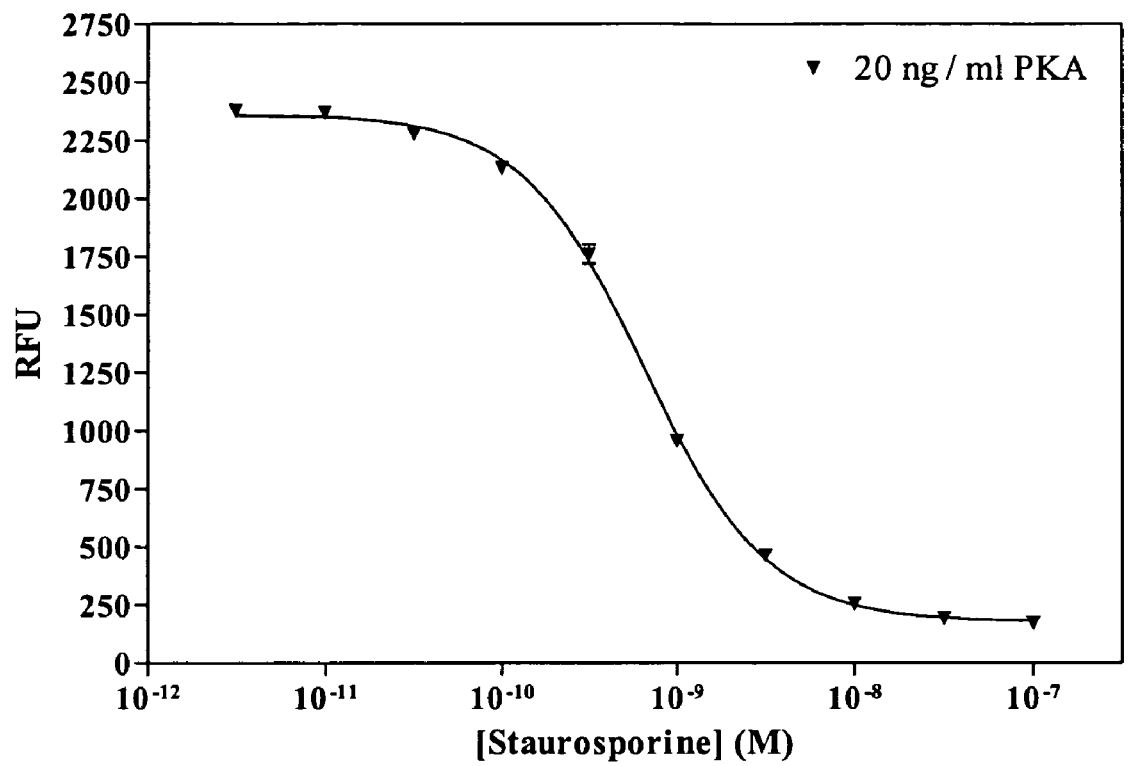
FIG. 5 is an inhibition curve for staurosporine and PKA.

Titration of staurosporine resulted in a dose dependent inhibition of PKA activity with an $IC_{50}$ of 0.6 nM (FIG. 5).

It is evident from the above results that an improved sensitive determination of ADP is provided that is substantially free of interference from entities involved in the determination. Furthermore, the correcting components that are added do not interfere with the sensitivity of the assay nor introduce artifacts that might give spurious results. The correcting components act in concert with the reagents in inhibiting erroneous results from the adventitious presence of compounds associated with the ADP determination. While the number of reagents employed for the determination in conjunction with the correcting components, the assay is simple since a large proportion of the reagents and correcting components can be combined in a single reagent avoiding the introduction of errors resulting from the measurement and transfer of individual reagents.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. In a method for determining ATPase activity in a sample by measuring ADP to estimate the extent of reaction of ATP, where the method comprises the steps of: combining the sample, with reagents comprising ATP, pyruvate kinase, phosphoenolpyruvate, pyruvate oxidase and agents for determining the production of hydrogen peroxide from the reaction of pyruvate catalyzed by pyruvate oxidase, said agents producing a detectable product; and determining said detectable product;

the improvement which comprises:
prior to adding the ATP and said sample to said reagents, combining catalase or peroxidase and a non-interfering substrate with said reagents other than ATP and at least one of:
1) with said ATP, correcting components selected from the group consisting of (a) creatine phosphokinase and phosphocreatine and (b) pyruvate kinase and phosphoenolpyruvate, or
(2) with said phosphoenolpyruvate, correcting components selected from the group consisting of (a) lactate dehydrogenase (LDH) and reduced nicotinamide adenine dinucleotide (NADH), (b) glutamic pyruvic transaminase and glutamic acid and (c) pyruvate oxidase and wherein the amounts employed of said correcting components are substantially non-interfering in said determining of ATPase activity.

2. A method according to claim 1 wherein said phosphoenolpyruvate is combined with a member of the group consisting of
(1) lactate dehydrogenase and reduced nicotinamide adenine dinucleotide,
(2) glutamic pyruvate transaminase and glutamic acid and
(3) pyruvate oxidase.

3. A method according to claim 1, wherein substantially non-interfering is that the difference in the observed results in the presence of the correcting components and in their absence with non-contaminated reagents is less than about 10%.

4. A method according to claim 3, wherein said reagents further comprise peroxidase, where said reagents and correcting components are at a concentration in the range of:

| Component | Range |
| --- | --- |
| Pyruvate kinase | 5-500 U/ml |
| Pyruvate oxidase | 1-100 U/ml |
| Peroxidase | 1-100 U/ml |
| Catalase | 0.01-10 U/ml |
| Phosphoenolpyruvate | 10-1000 µM. |

5. A method according to claim 3, wherein said reagents and correcting components further comprise peroxidase, FAD, TPP, buffer, peroxidase substrate, and activating salt, where said reagents are at the concentration ranges indicated:

| Component | Range |
| --- | --- |
| Pyruvate kinase | 5-500 U/ml |
| Pyruvate oxidase | 1-100 U/ml |
| Peroxidase | 1-100 U/ml |
| Catalase | 0.01-10 U/ml |
| Flavin adenine dinucleotide (FAD) | 1-100 µM |
| Thiamine pyrophosphate (TPP) | 10-1000 µM |
| Phosphoenolpyruvate | 10-1000 µM |
| Buffer | 10-100 mM |
| Peroxidase substrate | 10-100 µM |
| Activatin salt (e.g., $MgCl_2$) | 0.2-40 mM. |

6. A method according to claim 3, wherein said reagents and correcting components further comprise peroxidase, FAD, TPP, buffer, peroxidase substrate, activating salt, and enzyme stabilizer, where said reagents are combined in a single reagent comprising the composition:

| Component | Range |
|---|---|
| Pyruvate kinase | 10-500 U/ml |
| Pyruvate oxidase | 2-50 U/ml |
| Peroxidase | 1-50 U/ml |
| Catalase | 0.02-10 U/ml |
| Flavin adenine dinucleotide (FAD) | 2-80 μM |
| Thiamine pyrophosphate (TPP) | 20-500 μM |
| Phosphoenolpyruvate | 20-800 μM |
| Buffer | 10-100 mM |
| Activatin salt (e.g., MgCl$_2$) | 0.2-30 mM. |
| Enzyme stabilizer | 2-40 wt %. |

* * * * *